US012685575B2

(12) United States Patent
Germaneau et al.

(10) Patent No.: US 12,685,575 B2
(45) Date of Patent: Jul. 21, 2026

(54) DEVICE FOR HELPING TO BEND SURGICAL RODS

(71) Applicants: UNIVERSITE DE POITIERS, Poitiers (FR); CENTRE NATIONAL DE LA RECHERCHE SCIENTIFIQUE—CNRS, Paris (FR); CENTRE HOSPITALIER UNIVERSITAIRE DE POITIERS, Poitiers (FR)

(72) Inventors: Arnaud Germaneau, Miganloux Beauvoir (FR); Tanguy Vendeuvre, Poitiers (FR)

(73) Assignees: UNIVERSITE DE POITIERS, Poitiers (FR); CENTRE NATIONAL DE LA RECHERCHE SCIENTIFIQUE—CNRS, Paris (FR); CENTRE HOSPITALIER UNIVERSITAIRE DE POITIERS, Poitiers (FR)

( * ) Notice: Subject to any disclaimer, the term of this patent is extended or adjusted under 35 U.S.C. 154(b) by 258 days.

(21) Appl. No.: 18/549,300

(22) PCT Filed: Mar. 7, 2022

(86) PCT No.: PCT/FR2022/050406
§ 371 (c)(1),
(2) Date: Sep. 6, 2023

(87) PCT Pub. No.: WO2022/189745
PCT Pub. Date: Sep. 15, 2022

(65) Prior Publication Data
US 2024/0173059 A1 May 30, 2024

(30) Foreign Application Priority Data
Mar. 8, 2021 (FR) ...................................... 2102186

(51) Int. Cl.
A61B 17/88 (2006.01)
A61B 17/56 (2006.01)
A61B 34/10 (2016.01)

(52) U.S. Cl.
CPC .......... *A61B 17/8863* (2013.01); *A61B 34/10* (2016.02); *A61B 2017/568* (2013.01); *A61B 2034/102* (2016.02); *A61B 2034/105* (2016.02)

(58) Field of Classification Search
CPC .......... A61B 17/8863; A61B 2017/568; A61B 2034/102; A61B 2034/105; A61B 2034/108; A61B 34/10; A61B 34/20
See application file for complete search history.

(56) References Cited

U.S. PATENT DOCUMENTS

| | | | |
|---|---|---|---|
| 10,318,655 B2 | 6/2019 | Mosnier et al. | |
| 10,405,935 B2 | 9/2019 | Mcgahan et al. | |

(Continued)

FOREIGN PATENT DOCUMENTS

| | | |
|---|---|---|
| FR | 3010628 | 3/2015 |
| WO | 2013191980 | 12/2013 |

OTHER PUBLICATIONS

International Search Report for application No. PCT/FR2022/050406 dated Jun. 3, 2022.

(Continued)

*Primary Examiner* — Samuel S Hanna
(74) *Attorney, Agent, or Firm* — Perman & Green, LLP

(57) ABSTRACT

A method for helping to bend a rod that can be implanted in a patient, the method including the following steps: acquiring one or more measurements of distance and/or angle between elements of a vertebral column of the patient; determining a type of vertebral column of the patient, on the basis of the measurements, according to a classification; identifying one or more invariant parameters corresponding (Continued)

to the determined type of vertebral column; calculating one or more radii of curvature for bending a rod on the basis of the previously identified invariant parameters and the determined type of vertebral column; obtaining a representation of the rod bent according to the one or more radii of curvature; and displaying the representation.

11 Claims, 5 Drawing Sheets

(56) References Cited

U.S. PATENT DOCUMENTS

| | | |
|---|---|---|
| 2009/0249851 A1 | 10/2009 | Isaacs |
| 2015/0320471 A1 | 11/2015 | Crawford et al. |
| 2018/0289396 A1 | 10/2018 | Mcgahan et al. |
| 2019/0336179 A1 | 11/2019 | Pak et al. |
| 2020/0015857 A1 | 1/2020 | Rout et al. |
| 2020/0060768 A1 * | 2/2020 | Mosnier .................. G06T 7/337 |

OTHER PUBLICATIONS

Pierre Roussouly, MD, et al., "Classification of the Normal Variation in the Sagittal Alignment of the Human Lumbar Spine and Pelvis in the Standing Position", SPINE vol. 30, No. 3, pp. 346-353, 2005, Copyright © Lippincott Williams & Wilkins, Inc.

* cited by examiner 21
20
22

DEVICE FOR HELPING TO BEND SURGICAL RODS

CROSS REFERENCE TO RELATED APPLICATIONS

This application is a National Stage of International Application No. PCT/FR2022/050406, having an International Filing Date of 7 Mar. 2022, which designated the United States of America, and which International Application was published under PCT Article 21(2) as WO Publication No. 2022/189745 A1, which claims priority from and the benefit of French Patent Application No. 2102186 filed on 8 Mar. 2021, the disclosures of which are incorporated herein by reference in their entireties.

BACKGROUND

Field

The present disclosure relates to the field of implanting medical implants and is more particularly concerned with a device that allows the bending of rods used for spinal surgery and seeks to assist a surgeon or practitioner in the bending of implantable rods as a function of morphological characteristics of a patient.

Brief Description of Related Developments

For certain pathologies, it is known practice to use medical implants during surgical operations in order to correct and/or stabilize, either temporarily or permanently, the spinal column of a patient. The medical implants may for example consist of rods fixed to various fixation points of the spinal column using hooks, screws or other means.

Before being implanted in the patient, the rods need to be bent, which is to say deformed in one or more planes, in order to give them a specific curvature suited to the anatomical curvature of the patient.

At the present time, the bending of implantable rods is performed predominantly by hand by the surgeon during the course of the surgical operation, which means that most of the time it is not possible to obtain optimal correction through the sole use of clinical examination or medical images of the patient and without access to customized models.

Pre-bent rods, possibly custom-bent, that the surgeon does not need to bend themself also exist. However, these pre-bent rods are able to account for only certain anatomical curvatures determined in advance which are not necessarily entirely suitable for a specific patient.

In the case of a custom pre-bent rod, if there are problems with orders or delivery or if the rod becomes non-sterile during surgery before it is implanted, the operation may be compromised.

In order to alleviate these disadvantages, there are solutions aimed at customizing the bending of the rod to a greater extent to suit the patient concerned.

Document WO2013/191980 A1 describes a method for producing an implantable rod which involves attaching fixings to the spinal column of a patient beforehand. The curvature of the rod can be determined using a probe that locates the position of the fixings. However, this solution entails determining the bending of the rod once the dorsal fixings have already been attached during the surgical operation. It is complex to implement and entails guaranteeing the sterility of the probe and lengthens the intervention time.

Document U.S. Pat. No. 10,405,935 B2 describes a device for bending a rod on the basis of a digitization system that measures the shape of the spinal column of a patient and controls a bending machine. This device is complex and expensive; many hospitals are unable to acquire the associated bending machine.

There is therefore currently no solution that is simple, easy to use and suitable for creating rods that have been bent into shape in an optimized and customized way.

SUMMARY

In light of the prior art, the present application proposes first of all a method for helping with bending a rod that can be implanted in a patient, the method comprising, on the basis of a prior acquisition of one or more measurements of distance and/or of angle between elements of a spinal column of the patient, these measurements being taken from an image of the back of the patient, the following steps:

a. determining a type of spinal column of the patient according to a classification;

b. identifying one or more invariable geometrical parameters corresponding to the type of spinal column determined;

c. calculating one or more radii of curvature for the bending of a rod as a function of said measurements, of the type of spinal column determined and of said invariable parameters previously identified;

d. obtaining a representation of the rod bent to said one or more radii of curvature; and e. displaying the representation.

Such a method allows the practitioner to create and implant a bent rod suited to the patient at the time of an intervention.

Advantageously, said distance and/or angle measurements may comprise at least the measurement of a distance between vertebrae L4 and S1 and/or the distance between vertebrae L1 and S1 of the patient.

Said invariable parameters may comprise a pelvis parameter and an inter-vertebrae distance.

Said distance and/or angle measurements may comprise a pelvic tilt measurement.

The method may comprise classifying the spinal column according to a type selected from four types of spinal column defining models of lumbar lordosis, thoracic kyphosis, cervical lordosis, cervical kyphosis so as to refine the bending performed.

Advantageously, the method may comprise an algorithm implementing a bending-calculation formula including the invariable parameters of said geometric invariables associated with said types of spinal column.

The calculation for determining a geometry(s) for the bending of the rod may notably be of the form:

$$s = f_n(q_i)$$

the parameters $q_i$ being dependent on the measurements, on the type of spinal column and on invariables according to the types of spinal column.

More specifically, a radius of curvature for the bending of the rod may be calculated according to the following formula:

$$s = B(q_i) \cdot \left(1 - A(q_i) \cdot x^2\right)^{\frac{1}{2}}$$

[Math 1]

3 where the coefficients $A(q_i)$ and $B(q_i)$ are determined on the basis of the measurements acquired, of the type of spinal column and of said invariable parameters, and x is the spatial coordinate of the rod curvature in the picture or the projection.

The method may comprise the calculation of several successive radii of curvature of the rod.

The function $f_n(q_i)$ may also be produced from equations of circles, of ellipses, or of combinations of splines.

The equation or equations may be integrated into the memory of the device.

Said equations may also be adapted by the surgeon or the practitioner using a specific formula.

According to a variant, the invariable parameters may be identified on the back of the patient or on at least one image of the back of the patient in a sagittal plane.

The disclosure further proposes a device for helping with bending a rod that can be implanted in a spinal column of a patient, comprising:

a. acquisition means configured to acquire, from an image of the back of the patient, one or more measurements of distance and/or of angle between elements of the spinal column of the patient;

b. storage means configured to store a classification of types of spinal column and invariable parameters, c. processing means configured to:

i. determine a type of spinal column of the patient according to a determined classification;

ii. identify one or more invariable parameters corresponding to the type of spinal column determined;

iii. calculate one or more radii of curvature for the bending of a rod as a function of said measurements, of the invariable parameters previously identified, of the type of spinal column determined and of calculation parameters;

iv. obtain a representation of the rod bent according to said one or more radii of curvature;

d. display means configured to display the representation.

The device thus makes it possible to model a bent rod directly at the time of an intervention on the basis of patient data obtained during the intervention or during a preoperation phase.

The device may further comprise a previously-constructed database connecting said types of spinal column, geometric links, invariable parameters and containing equations suited to said types of spinal column for calculating said model of the back of the patient and said bending.

BRIEF DESCRIPTION OF THE DRAWINGS

Further features, details and advantages of the disclosure will become apparent from reading the detailed description below, and from analyzing the attached drawings, in which.

DESCRIPTION OF THE ASPECTS

The drawings and the description which follow contain elements which serve not only to make the present disclosure easier to understand, but also to contribute to the definition thereof, where applicable.

The present disclosure seeks to assist a surgeon or practitioner in the bending of rods as a function of the morphological characteristics of a patient. It may be used in particular for any osteosynthesis of the spinal column that entails the positioning and fixing of screws, plates, nails, rods, etc., implanted internally, within the bone, or externally with the aid of external fixators.

It may notably be used in particular for spinal arthrodesis.

As described hereinafter, the surgeon or practitioner may, thanks to the disclosure, preoperatively and/or peroperatively visualize and plan the bending of the rod that is to be performed for a given patient.

"Preoperatively" and "peroperatively" are to be understood respectively as meaning planning prior to surgery (with the patient conscious) and planning during the surgery (with the patient unconscious).

Figure 1:
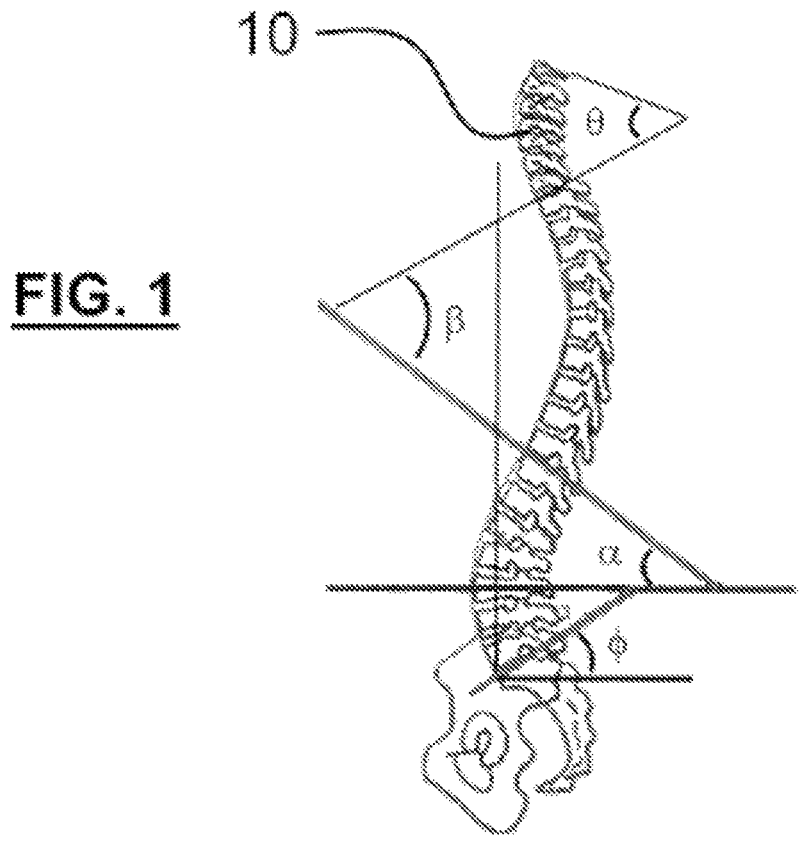
FIG. 1 shows a schematic view of a spinal column and of the characteristic curvatures thereof.

The spinal column 10 generally exhibits a number of curvatures in the sagittal plane, as depicted in FIG. 1. These curvatures notably define lumbar lordosis a, thoracic kyphosis β and three possible types of cervical curvature θ (lordosis, kyphosis and neutral), as well as sacral kyphosis φ.

Figure 2:
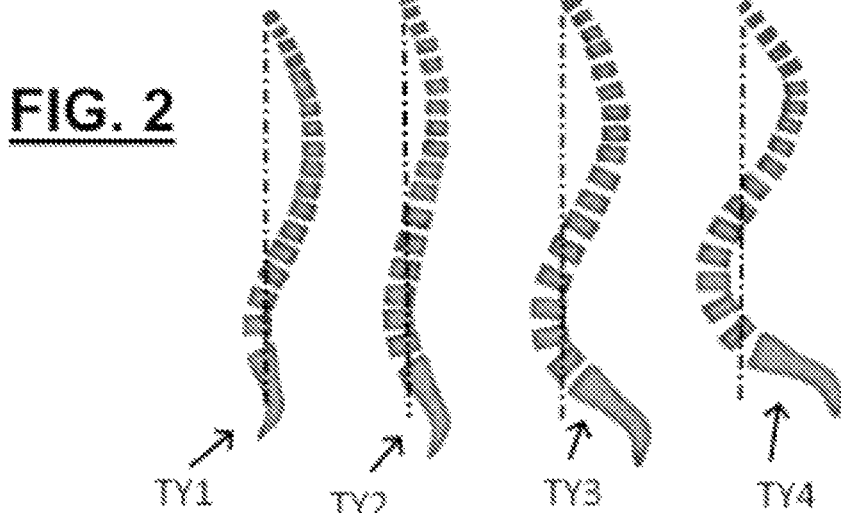
FIG. 2 shows a classification of different types of spinal column.

There are thus four main types of spinal column, referred to as TY1, TY2, TY3, TY4 as depicted in FIG. 2 (Roussouly et al, SPINE, Vol. 30, 3, p. 346-353, 2005). It is generally accepted that type TY3 is the usual shape of the spinal column. Types TY1, TY2 and TY4 relate to curvatures liable to arise from certain pathologies or to encourage certain pathologies. The spinal column of a given patient may therefore be examined so as to be categorized according to a particular type.

For each of these types of spinal column, it is possible to define geometrical measurements on the basis of which invariable parameters may be identified.

What is meant by "geometrical measurements" is a measurement of distance or of angle connecting two or more elements of the spinal column. One element of the spinal column may be the position of a vertebra, the plane of separation between two vertebrae or, more generally, any particular position of the spinal column.

Thus, one invariable parameter identified may consist of a measurement of the distance or angles, in one or more planes, between elements of the spinal column. An invariable parameter may notably be chosen from among lumbar lordosis, thoracic kyphosis and cervical curvature and sacral kyphosis as illustrated in FIG. 1. However, other invariable parameters are possible.

Figure 3:
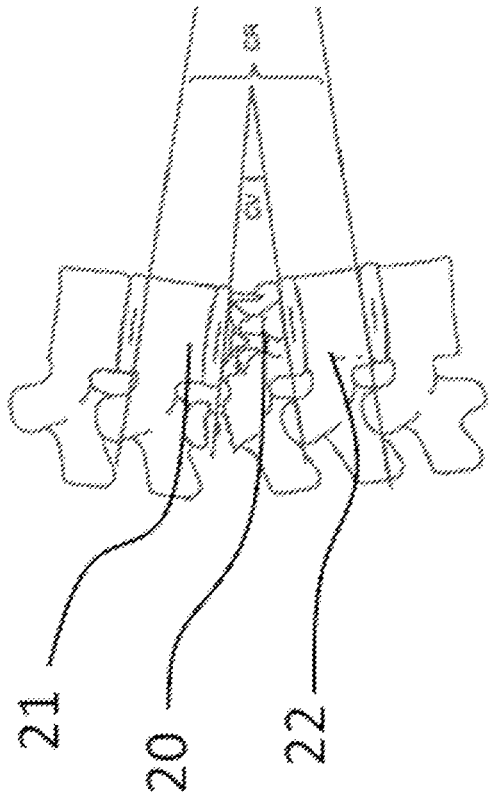
FIG. 3 shows a detail of the mutual angulation of vertebrae of a spinal column.

On the basis of the type of spinal column and of the invariable parameters identified, the present disclosure makes it possible to define optimal angulations that the spinal column needs to satisfy in order to correct the pathology of the patient. In this context, FIG. 3 depicts a part of the spine with an injury at vertebra 20 where the regional kyphosis angulations CR between vertebrae 21 and 22 flanking vertebra 20 and the vertebral kyphosis CV need to be reestablished in order to restore the regional angulation at the injury site to a physiological angulation suited to the position of the vertebrae (for example 9° for T11, 7° for T12, 1° for L1, 8° for L2; 18° for L3, etc).

What is meant by optimal angulation is the angulation of the spinal column that is customized for a given patient in order to best restore the posture of said patient to a position of stable equilibrium.

The bent rod that needs to be implanted in the patient may thus be adapted to these angulations. The surgeon or practitioner may, before or during the surgical operation, bend the rod in a way that is customized and specific to the patient in order to best restore the (lordosis or kyphosis) angulations.

Thus, the disclosure relates to a device and a software package enabling the calculation of the curvature or curvatures (or radii of curvature) of the rod that are needed for on the basis of the model of the spinal column and of the invariable parameters of a patient.

In particular, the device makes it possible to provide a representation of the bent rod specific to the patient. The representation may advantageously be produced in real time and on a scale of 1:1 (life size) using any display means.

What is meant by "in real time" is notably that the disclosure may be carried out before but also during the surgical operation so that the rod can be bent during the operation time.

The simulated representation of the bent rod on a scale of 1:1 simplifies the task of the surgeon who can easily compare the rod that the surgeon has actually bent/has to bend with the representation obtained using the device according to the disclosure.

The surgeon can thus rely on this representation to then perform the bending of the rod using a dedicated bending device, also known as a bender.

According to one aspect, the surgeon therefore has access to a straight rod and to a bender (which is a device commonly used in the operating theater) but which is color coded according to three degrees of bending provided by three rollers, these bending rollers being color coded to define three curvatures. The device of the disclosure will supply the appropriate code so that the practitioner can select the correct configuration for the bender according to circumstance.

Figure 6:
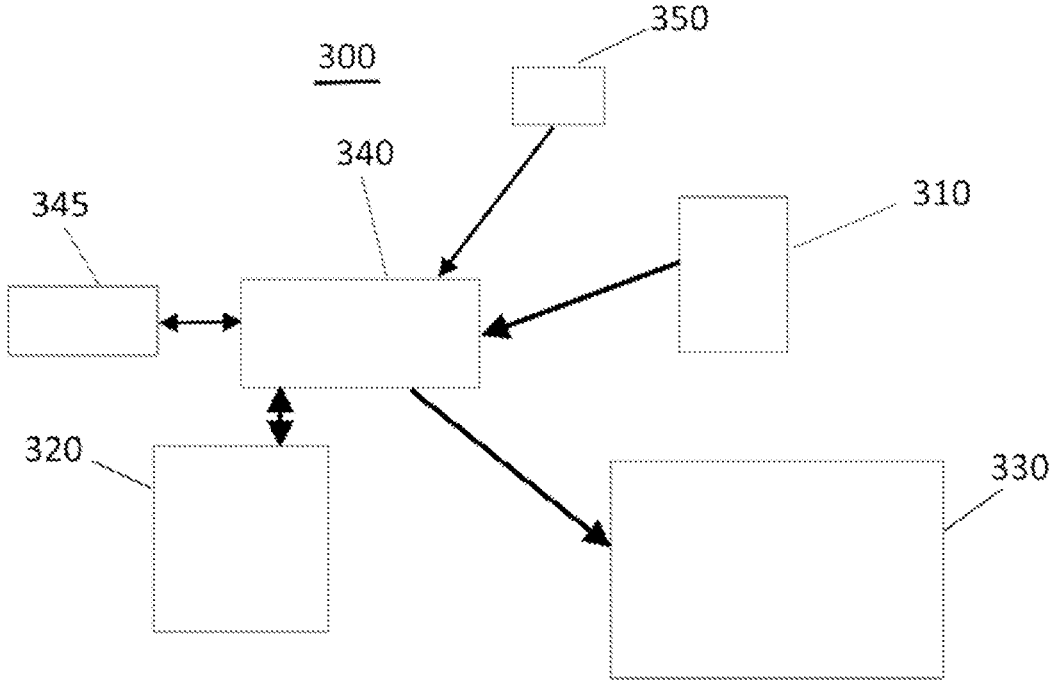
FIG. 6 is a schematic depiction of a device according to the disclosure.

The device for helping with bending according to the disclosure and schematically depicted in FIG. 6 will be described hereinafter.

The device for helping with bending 300 comprises acquisition means 310 configured to acquire the measurements of distance and/or of angle between the elements of the spinal column.

The acquisition or interface means 310 may for example take the form of a human-machine interface that allows a surgeon or practitioner to input the distance and/or angle measurements for themself. According to another aspect, the distance or angulation measurements are obtained directly by importing medical images, such as radiographs, MRI, ultrasound or other images, produced using a medical imaging apparatus integrated into the device or sited elsewhere.

The device further comprises storage or memory means 320 able to store the medical images or the measurements acquired by the acquisition means of the device. The memory also contains a classification of models of spinal column as well as the invariable parameters associated with each type of spinal column.

The device further comprises processing or computer means 340, 345, such as a processor and its random access memory. As detailed hereinafter, the processing means are able to implement the method according to the disclosure in order to obtain the optimal angulations that the rod, once bent, needs to meet.

The device comprises a display module 330, for displaying, notably at a scale of 1:1, the curvature of an implantable rod so as to allow a surgeon to bend said rod, for example during the course of a surgical intervention. These means may comprise, for visualizing the bending of the rods, at least one of a tablet, a flat screen, a device for projecting video onto a table, a virtual reality headset or any other known display device.

Furthermore, by using, during the operation, implants (screws, hooks, clamps) which, once locked, are perpendicular to the rod and parallel to the upper surfaces of the vertebrae, it is then possible to define the angulation between these implants and to estimate, as a function of the distance between these implants, the bending to be performed in order to adjust the radius of curvature to suit the angulation. In that case, the disclosure may be used as a peroperative planning tool by directly measuring the distance between the vertebrae of the patient during the course of the operation. The device of the disclosure makes it possible to optimize the manual bending performed with the tools usually employed by surgeons (bending irons, pliers, etc.) and is compatible with the various ancillaries currently used in operating theaters.

The device and the method make it possible to calculate the curvatures for different types of rod, for example in the case of injury or of a degenerating segment, the practitioner will ask the tool to calculate for a short rod fusing 2 to 5 vertebrae. By contrast, in the case of sagittal deformation or imbalance, the rods will be longer involving 5 to 26 vertebrae and, in that case, a number of successive curvatures will be calculated using the method of the disclosure.

Figure 4:
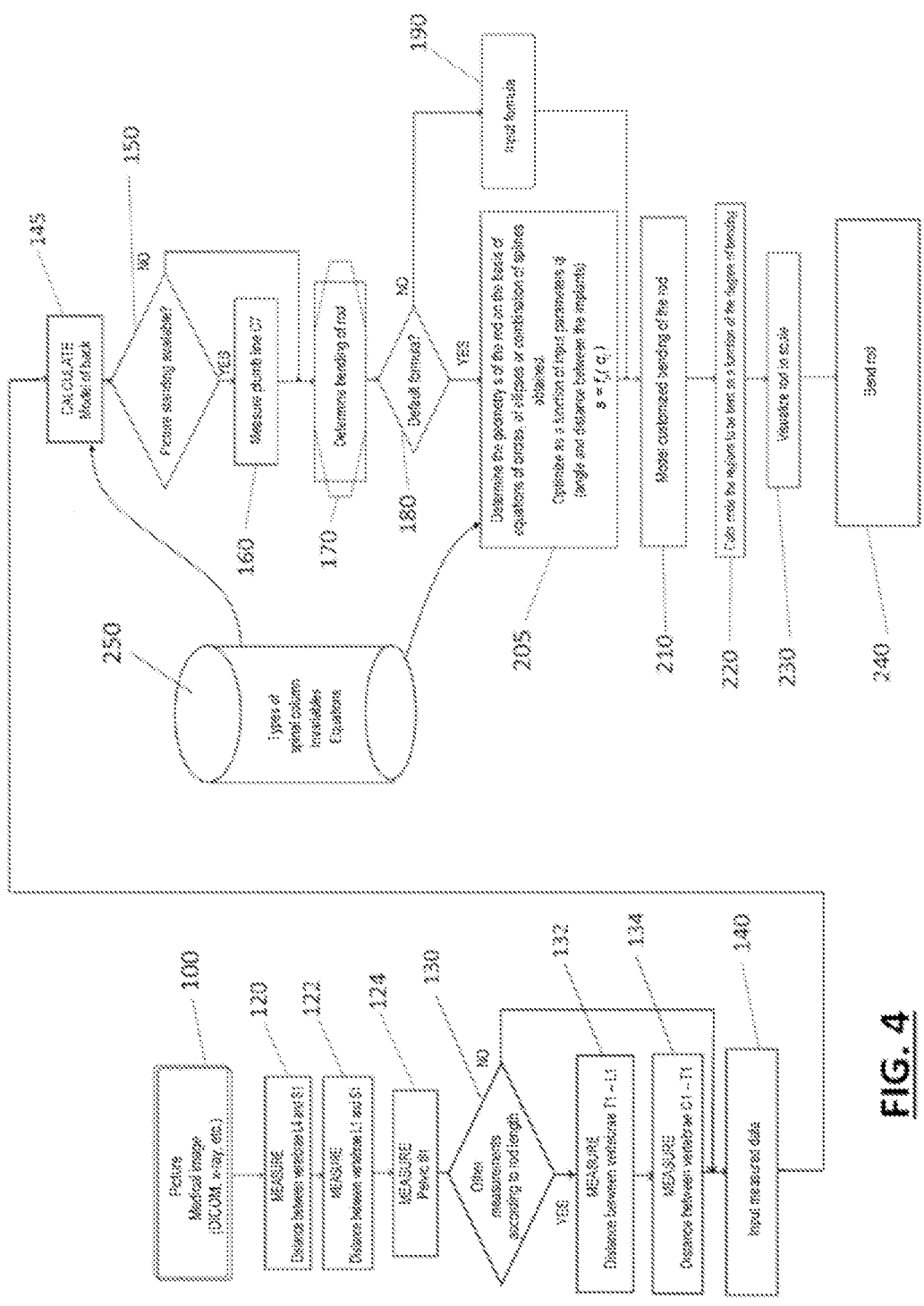
FIG. 4 is a flow diagram exemplifying the disclosure according to a first aspect.

The flow diagram of FIG. 4 provides one example of the implementation of the method according to a first aspect of the disclosure.

A step 100 consists in acquiring medical images.

In one or more subsequent steps, the practitioner takes measurements on the basis of the medical images previously acquired. According to the first aspect, the measurements may be measurements of distance between vertebrae L4 and S1, step 120, between vertebrae L1 and S1, step 124, and measurement of pelvic tilt, step 126. However, the disclosure is not restricted to these distance measurements and other measurements may be taken, between different elements of the spinal column. In particular, if the rod needs to extend toward the top of the spinal column, measurements of the distance T1-L1, if the rod extends into the thorax, then CO-T1, if the rod extends into the cervical spine may be needed. In that case, the measurements may be performed after a test 130 and may comprise a measurement 132 between thoracic vertebra T1 and lumber vertebra L1 for a rod extending into the thorax, then a measurement between thoracic vertebra T1 and cervical vertebra CO in step 134.

In a step 140, the measurements are input into the device and, in a step 145, the device classifies the spinal column. In particular, the calculation makes it possible to determine the type of spinal column of the patient, for example from among the various types of spinal column TY1, TY2, TY3, TY4 described above which may be grouped with other data such as invariables and equations that can be used, in a database 250.

After the step 140, one or more additional measurements may potentially be taken. These additional measurements may notably comprise a plumb-line measurement at vertebra C7 if an image of the patient in a standing position is available (steps 150, 160).

Other information may also be input into the device, for example the type of rod concerned, the presence and position of other implants, etc.

In a process 170, the method comprises an algorithm that implements a bending calculation formula that includes the invariable parameters of said geometric invariables associated with said types of spinal column.

According to the example of FIG. 4, the method involves calculation to determine the bending of the rod. This calculation is performed here in step 200 wherein the geometry:

$$s = f_n(q_i)$$ [Math 2]

of the rod is determined on the basis of equations of circles, of ellipses or of combinations of splines and as a function of parameters qi that are dependent on the measurements, on the type of spinal column, and on invariables according to the type of spinal column.

The equations may be integrated into a memory of the associated device or may potentially be adapted by the surgeon or the practitioner by means of a specific formula 190, according to the choice made in step 180.

Next, the device:
e.—produces a 1:1-scale model 210;
f.—provides the color codes 220 for the various bending means suitable for performing the bending of the rod;
g.—represents 230 the rod on a scale of 1:1 using the display means.

The practitioner may then, in step 240, bend the rod directly on the specific bending device provided with the appropriate bending means. This device may notably be equipped with bending means comprising color codes according to their curvature that have the same color as the colors derived from the model.

Figure 5:
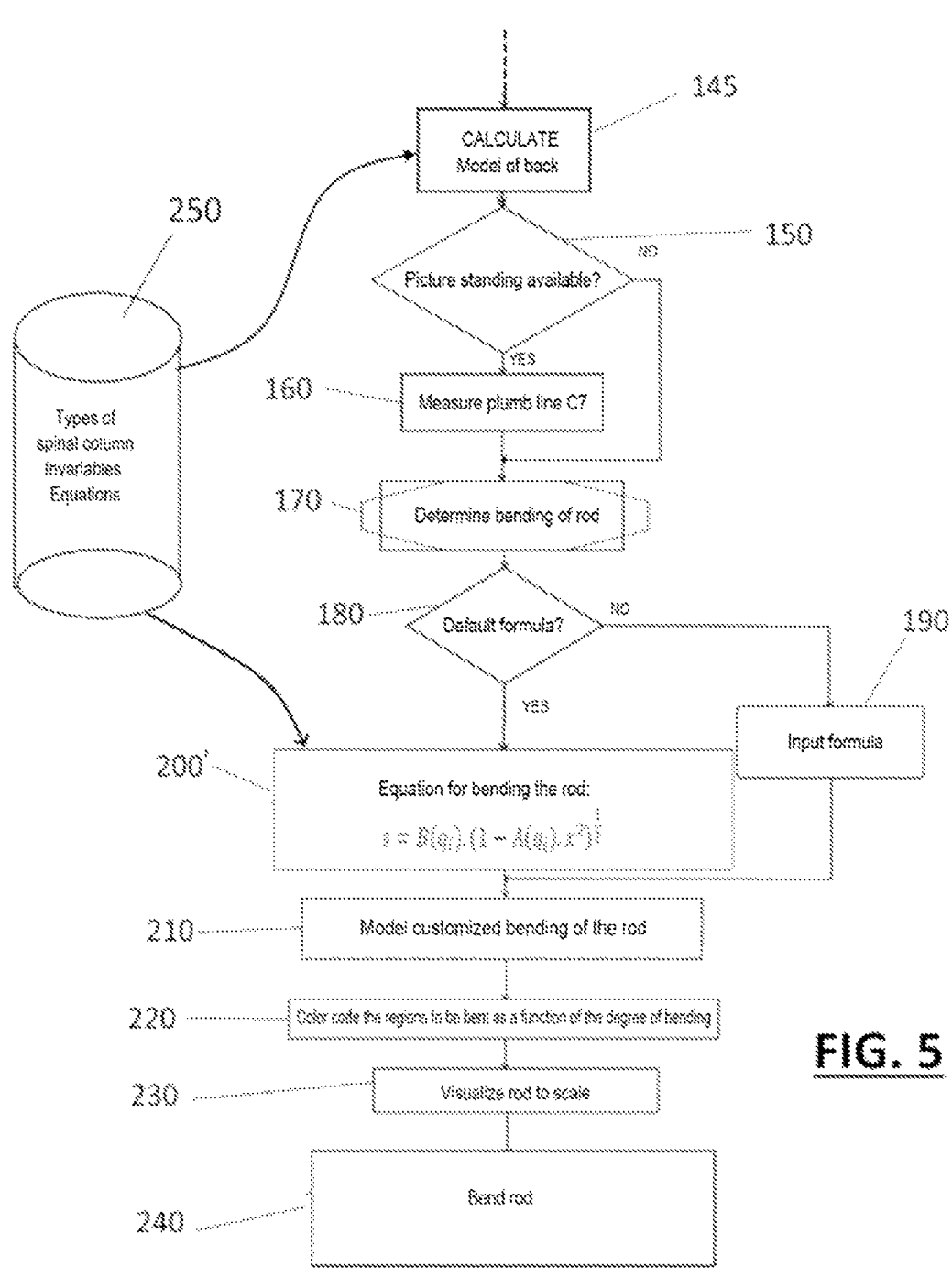
FIG. 5 is a flow diagram exemplifying steps of the disclosure according to a second aspect.

In the variant of FIG. 5 which resumes the steps starting from step 145, there is a particular bending calculation equation whereby the bending s corresponds to the formula:

$$s = B(q_i) \cdot \left(1 - A(q_i) \cdot x^2\right)^{\frac{1}{2}}$$ [Math 3]

In this equation, the coefficients A(qi) and B(qi) are determined on the basis of the measurements 120, 122, 124 and potentially 132, 134 and of the type of spinal column, and x is the spatial coordinate of the curvature of the rod in the picture or the projection. The origin for the coordinates is fixed at vertebra S1. The parameters qi represent the anatomical input data measured by the surgeon (inter-vertebrae distances, pelvic tilt).

When the rod needs to have several curvatures, the equation defining it is adapted to produce the curvatures of various segments of the rod, for example lumbar segment, thoracic segment and/or cervical segment and several successive calculations of the radii of curvature of the rod may be performed in order to model the rod.

The disclosure is not restricted to the examples described hereinabove, solely by way of example, but it encompasses all variants that a person skilled in the art might envision within the scope of the protection defined by the claims and, in particular, the device may comprise means for viewing on a 1:1 scale that are other than those described.

What is claimed is:
1. A method for helping with bending a rod that can be implanted in a patient, the method comprising, on the basis of a prior acquisition of one or more measurements of distance and/or of angle between elements of a spinal column of the patient, these measurements being taken from an image of the back of the patient, the following steps:
   a) determining a type of spinal column of the patient according to a classification;

b) identifying one or more invariable geometrical parameters corresponding to the type of spinal column determined;
   c) calculating one or more radii of curvature for the bending of a rod as a function of said measurements, of the type of spinal column determined and of said invariable geometrical parameters previously identified;
   d) obtaining a representation of the rod bent to said one or more radii of curvature; and
   e) displaying the representation at a scale of 1:1,
   said method comprising an algorithm implementing a bending-calculation formula including invariable parameters of said invariable geometrical parameters associated with said types of spinal column and wherein a radius of curvature s for the bending of the rod is calculated according to the following formula:

$$s = B(q_i) \cdot \left(1 - A(q_i) \cdot x^2\right)^{\frac{1}{2}}$$

where the coefficients $A(q_i)$ and $B(q_i)$ are determined on the basis of the measurements acquired, of the type of spinal column and of said invariable parameters, and x is the spatial coordinate of the rod curvature in the picture or the projection.

2. The method as claimed in claim 1, wherein said distance and/or angle measurements comprise at least the measurement of a distance between vertebrae L4 and S1 and/or the distance between vertebrae L1 and S1.

3. The method as claimed in claim 1, wherein the said invariable parameters comprise a pelvis parameter and an inter-vertebrae distance.

4. The method as claimed in claim 1, wherein said distance and/or angle measurements comprise a pelvic tilt measurement.

5. The method as claimed in claim 1, wherein the spinal column is classified according to a type selected from four types of spinal column (TY1, TY2, TY3, TY4) defining models of lumbar lordosis, thoracic kyphosis, cervical lordosis, cervical kyphosis and neutral.

6. The method as claimed in claim 1, wherein the calculation for determining a geometry(s) for the bending of the rod is of the form:

$$s = f_n(q_i)$$

the parameters $q_i$ being dependent on the measurements, on the type of spinal column and on invariables according to the types of spinal column.

7. The method as claimed in claim 6, wherein the function $f_n(q_i)$ is produced from equations of circles, of ellipses, or of combinations of splines.

8. The method as claimed in claim 7, wherein said equations are integrated into a memory of a device for helping with bending a rod that can be implanted in the spinal column of the patient.

9. The method as claimed in claim 7, wherein said equations are adapted by the surgeon or the practitioner using a specific formula.

10. The method as claimed in claim 1, comprising the calculation of several successive radii of curvature of the rod.

11. The method as claimed in claim 1, wherein said invariable parameters are identified on at least one image of the back of the patient in a sagittal plane.

* * * * *